United States Patent
Matsuura

(10) Patent No.: US 9,671,417 B2
(45) Date of Patent: Jun. 6, 2017

(54) ANALYZER AND ANALYZING METHOD

(71) Applicant: Sysmex Corporation, Kobe-shi, Hyogo (JP)

(72) Inventor: Hiroyuki Matsuura, Kobe (JP)

(73) Assignee: SYSMEX CORPORATION, Hyogo (JP)

( * ) Notice: Subject to any disclaimer, the term of this patent is extended or adjusted under 35 U.S.C. 154(b) by 0 days.

(21) Appl. No.: 14/226,465

(22) Filed: Mar. 26, 2014

(65) Prior Publication Data

US 2014/0295563 A1 Oct. 2, 2014

(30) Foreign Application Priority Data

Mar. 28, 2013 (JP) .................................. 2013-069967

(51) Int. Cl.
*G01N 35/04* (2006.01)
*G01N 35/02* (2006.01)

(52) U.S. Cl.
CPC ...... *G01N 35/04* (2013.01); *G01N 2035/0401* (2013.01); *G01N 2035/0465* (2013.01); *Y10T 436/114165* (2015.01)

(58) Field of Classification Search
CPC ......... Y10T 436/11; Y10T 436/113332; Y10T 436/114165; G01N 35/04; G01N 35/02; G01N 2035/0491; G01N 2035/0401; G01N 2035/0439; G01N 2035/0474
USPC ...................... 436/48, 47, 43; 422/63, 67, 50
See application file for complete search history.

(56) References Cited

U.S. PATENT DOCUMENTS

| | | | | |
|---|---|---|---|---|
| 5,333,716 A * | 8/1994 | Hoppmann | ........ | B65G 47/1471 198/380 |
| 5,359,907 A * | 11/1994 | Baker | ................ | G01N 15/0205 356/335 |
| 5,746,299 A * | 5/1998 | Molbak | .................... | G07D 3/14 194/200 |
| 6,119,737 A * | 9/2000 | Yuyama | .................. | B65B 5/103 141/104 |
| 6,284,459 B1 * | 9/2001 | Nova | ................... | B01J 19/0046 422/68.1 |
| 6,478,185 B2 * | 11/2002 | Kodama | ................. | B65B 5/103 221/13 |
| 7,348,182 B2 * | 3/2008 | Martin et al. | ................. | 436/518 |
| 2002/0106305 A1 | 8/2002 | Willenbring et al. | | |
| 2004/0131499 A1 | 7/2004 | Okada et al. | | |
| 2007/0269342 A1 | 11/2007 | Kitagawa | | |
| 2008/0063573 A1 * | 3/2008 | Ammann et al. | ............. | 422/105 |

(Continued)

FOREIGN PATENT DOCUMENTS

| | | |
|---|---|---|
| CN | 102621337 A | 8/2012 |
| JP | 60-242117 A | 12/1985 |
| JP | 03-085157 U | 8/1991 |

(Continued)

*Primary Examiner* — Christine T Mui
(74) *Attorney, Agent, or Firm* — Brinks Gilson & Lione

(57) ABSTRACT

There is provided an analyzer capable of stably supplying the cuvettes even if a great number of cuvettes is input to the storage section without thinking. The analyzer includes a storage section configured to store the plurality of input cuvettes, a take-out section configured to take out the cuvettes in the storage section from the storage section, and a vibration unit configured to vibrate the storage section to stimulate movement of the cuvettes in the storage section.

18 Claims, 11 Drawing Sheets

(56) References Cited

U.S. PATENT DOCUMENTS

| | | |
|---|---|---|
| 2009/0081081 A1 | 3/2009 | Kowari et al. |
| 2012/0171078 A1 | 7/2012 | Kaneko |

FOREIGN PATENT DOCUMENTS

| | | |
|---|---|---|
| JP | 05-022422 U | 3/1993 |
| JP | 06-032440 A | 2/1994 |
| JP | 07-160841 A | 6/1995 |
| JP | 07-206141 A | 8/1995 |
| JP | 08-091562 A | 4/1996 |
| JP | 08-198455 A | 8/1996 |
| JP | 2000-321286 A | 11/2000 |
| JP | 2001-027643 A | 1/2001 |
| JP | 2002-046842 A | 2/2002 |
| JP | 2007-061771 A | 3/2007 |
| JP | 2007-129052 A | 5/2007 |
| JP | 2009-074911 A | 4/2009 |
| JP | 2010-215408 A | 9/2010 |
| JP | 2011-209045 A | 10/2011 |

\* cited by examiner

ANALYZER AND ANALYZING METHOD

RELATED APPLICATIONS

This application claims priority under 35 U.S.C. §119 to Japanese Patent Application No. 2013-069967 filed on Mar. 28, 2013, the entire content of which is hereby incorporated by reference.

BACKGROUND OF THE INVENTION (1) Field of the Invention

The present invention relates to an analyzer including a storage section for storing a plurality of parts to be used in analyzing samples, the part being such as a container for preparing a specimen, and the like, and relates to an analyzing method.

(2) Description of Related Art

An analyzer including a storage section for storing a plurality of parts to be used in analyzing samples, the part being such as a container for preparing a specimen, and the like, and a supply mechanism section for supplying the plurality of parts toward an analyzing section one by one from the storage section is conventionally known.

US Patent Application publication No. 2002/106305 discloses a supply device, including a hopper (storage section) for storing a great number of containers input without thinking, for supplying the containers toward the analyzing section side one by one from the hopper. The supply device includes the hopper for storing the containers, a rotatable elevator chain including a plurality of scoopers, an escrow guide, and the like.

The containers positioned at the bottom of the great number of containers stored in the hopper are held by the scooper and transported to the upper side of the hopper by the elevator chain. The transported container is dropped onto the escrow guide so that the containers are transported out one by one from the escrow guide.

The great number of containers input without thinking into the hopper is concentrated at the bottom of the hopper, and thus the adjacent containers may be squeezed together and the containers may get tangled and become difficult to move due to the friction between the adjacent containers especially at the bottom. Thus, even if the container at the bottom is transported to the upper side by the elevator chain, if the other containers existing at the periphery of the relevant container are tangled and are difficult to move, the region where the container transported to the upper side existed remains as a space, and the transportation of the next container may not be satisfactorily carried out.

In this case, the container is not supplied toward the analyzing section side in the analyzer although the containers are present in the hopper, and the analyzing operation might be stopped.

SUMMARY OF THE INVENTION

The scope of the present invention is defined solely by the appended claims, and is not affected to any degree by the statements within this summary.

A first aspect of the present invention is an analyzer comprising:

a storage section configured to store a plurality of parts to be used in analyzing samples;

a take-out section configured to take out one or more of the plurality of parts from the storage section;

a vibration unit configured to vibrate the storage section to transmit vibration to the plurality of parts in the storage section; and an analyzing section configured to analyze a sample using at least one of the plurality of parts taken out by the take-out section.

A second aspect of the present invention is an analyzer comprising:

a storage section configured to store a plurality of parts to be used in analyzing samples;

a take-out section configured to take out one or more of the plurality of parts from the storage section;

a hitting unit configured to hit the storage section to transmit vibration to the plurality of parts in the storage section; and an analyzing section configured to analyze a sample using the at least one of the plurality of parts taken out by the take-out section.

A third aspect of the present invention is an analyzing method comprising:

vibrating a storage section storing a plurality of parts to be used in analyzing samples to transmit vibration to the plurality of parts in the storage section;

taking out one or more of the plurality of parts from the storage section; and analyzing a sample using at least one of the plurality of parts taken out.

DETAILED DESCRIPTION OF PREFERRED EMBODIMENTS

The preferred embodiments of the present invention will be described hereinafter with reference to the drawings.

An embodiment of the present invention will be hereinafter described based on the drawings.

[Overall Configuration of Analyzer 1]

Figure 1:
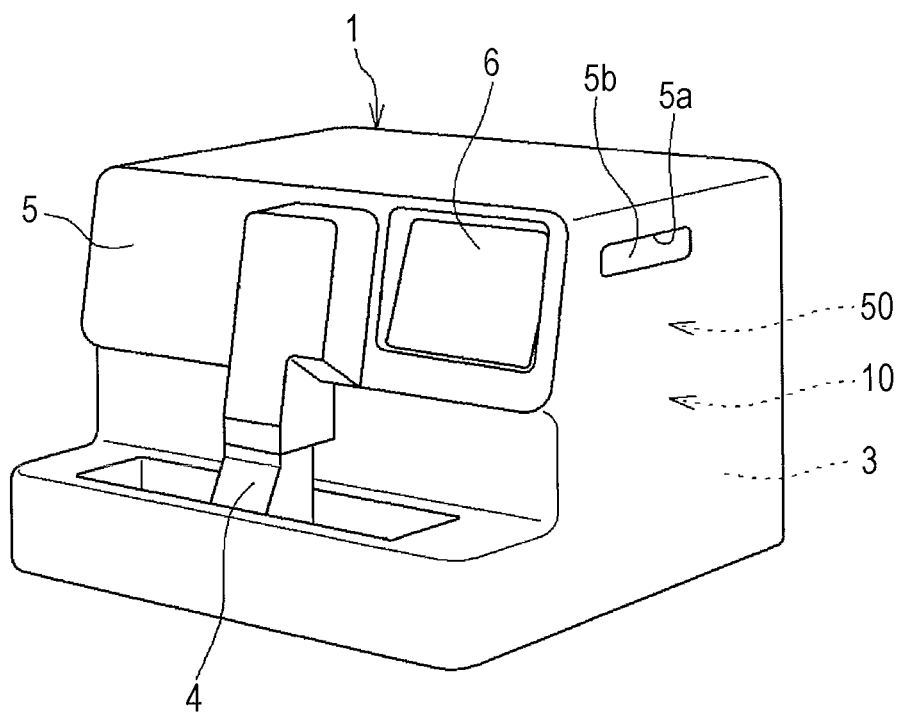
FIG. 1 is a perspective view of an analyzer according to the present invention.
Figure 2:
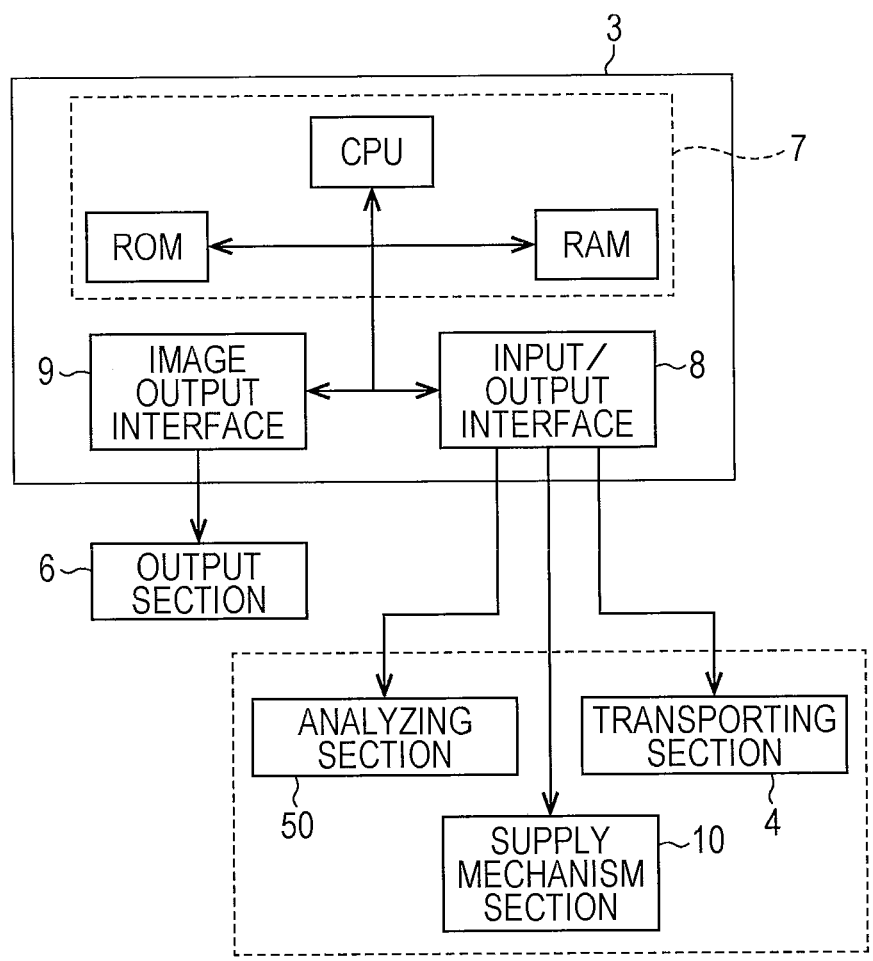
FIG. 2 is a block diagram of the analyzer.

As shown in FIG. 1 and FIG. 2, the analyzer 1 of the present embodiment includes an analyzing section 50 for analyzing samples, and a supply mechanism section 10 for supplying a cuvette 2 (see FIG. 9), which is a container containing the sample, to the analyzing section 50. The analyzer 1 of the present embodiment is a blood clotting analyzer for analyzing blood clotting reaction by applying a reagent to the blood sample contained in the cuvette.

As shown in FIG. 1, the analyzing section 50 and the supply mechanism section 10 are arranged in a housing 5 of the analyzer 1. A region where a plurality of test tubes containing samples is to be set is arranged at a front part of the housing 5 to supply the sample to the analyzing section 50. In this region, a transporting section 4 for transporting the test tube to the analyzing section 50 is provided.

The analyzer 1 further includes a control section 3 for performing the control of the operation of each mechanism unit of the analyzing section 50, the supply mechanism section 10, and the transporting section 4, and the process for analysis. In the present embodiment, the control section 3 is arranged in the housing 5, but may be arranged exterior to the housing 5. If arranged exterior to the housing 5, the control section 3 includes a personal computer, for example. An apparatus main body including the analyzing section 50, the supply mechanism section 10, and the transporting section 4 is connected to an interface of the personal computer.

The housing 5 includes an input port 5a, through which the user inputs the cuvette. The input port 5a includes an opening formed at the side surface of the housing 5. The cuvette is input into the housing 5 from such opening. The cuvette input through the input port 5a is placed in a storage section 11 (see FIG. 4), to be described later. Furthermore, the housing 5 includes a lid 5b that can open/close the input port 5a. The housing 5 also includes an output section 6 including a monitor for outputting information by character, and the like. The output section 6 can output various types of information as characters to the user.

In FIG. 2, the control section 3 includes a control unit 7 including a computer with a CPU, a ROM, a RAM, and the like, an output/input interface 8, and an image output interface 9.

The control unit 7 has a function of generating a command signal for operating the transporting section 4, the analyzing section 50, and the supply mechanism section 10, and transmits the command signal to each section through the output/input interface 8. The control unit 7 also has a function of receiving the signal output by the supply mechanism section 10 through the output/input interface 8, and generating a command signal for causing the output section 6 to output notification information, which is information urging replenishment of the cuvette 2, based on the signal. Furthermore, the control unit 7 has a function of receiving the signal output by the analyzing section 50, and carrying out the analyzing process based on the signal to generate analysis result information, which is information of a sample.

The command signal for outputting the notification information and the analysis result information are transmitted to the output section 6 through the image output interface 9. The output section 6 displays the received notification information, analysis result information, and the like.

Figure 3:
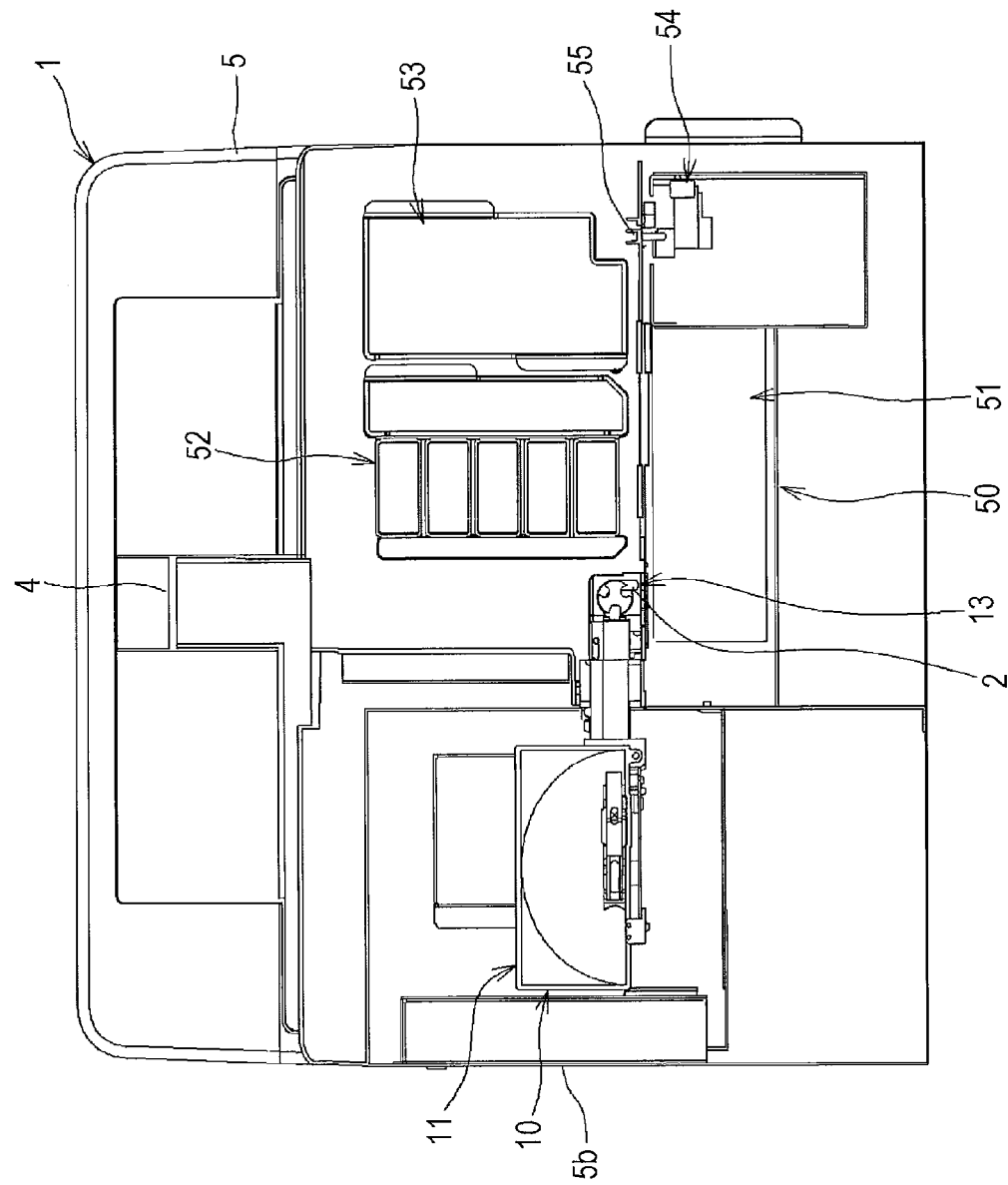
FIG. 3 is a plan view showing an outline of the configuration of the analyzer.

In FIG. 3, the front part side of the housing 5 is shown as the upper side. As shown in FIG. 3, the analyzer 1 includes the analyzing section 50 for performing an optical measurement with respect to the sample contained in the test tube transported by the transporting section 4. In the present embodiment, the analyzing section 50 includes a detection unit 51, a sample plate unit 52, a reagent installing unit 53, and a catcher device unit 54.

In the sample plate unit 52, the sample is dispensed from the test tube to the cuvette. The detection unit 51 includes a reaction bath for performing the optical measurement with respect to the dispensed sample. The catcher device unit 54 includes a grip portion 55 for gripping the cuvettes 2 supplied one by one by the supply mechanism section 10, where the grip portion 55 is moved to move the cuvette 2 from the supply mechanism section 10 to the detection unit 51. The reagent is installed in the reagent installing unit 53. In the process of moving from the supply mechanism section 10 to the detection unit 51, the sample is dispensed to the cuvette 2 gripped by the grip portion 55 in the sample plate unit 52, and furthermore, the reagent is dispensed by a reagent dispensing arm (not shown). Thereafter, the cuvette is moved to the detection unit 51.

In the detection unit 51, a measurement specimen, which is prepared by adding the reagent to the sample, is warmed, and the optical information is acquired from the measurement specimen. In the present embodiment, the optical measurement is carried out under a plurality of conditions with respect to the measurement specimen in the cuvette 2, and the acquired information is transmitted to the control unit 7. The control unit 7 analyzes the information transmitted from the detection unit 51 to obtain the analysis result. Such analysis result is output to the output section 6.

[Regarding Supply Mechanism Section 10]

Figure 9:
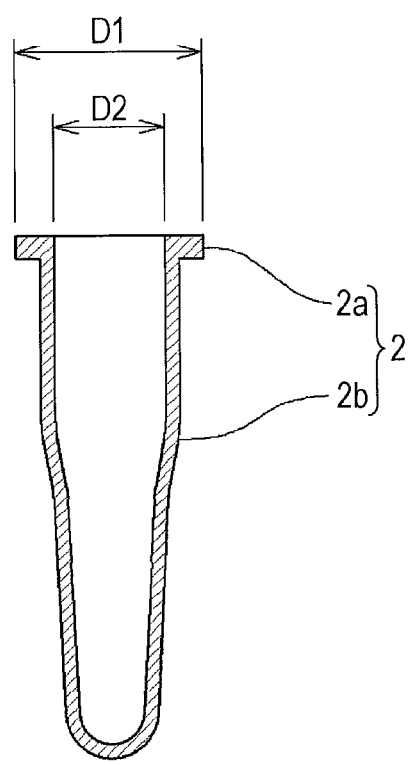
FIG. 9 is a cross-sectional view of a cuvette.

The supply mechanism section 10 is arranged to supply a plurality of cuvettes 2 (see FIG. 9) input without thinking by the user, to the analyzing section 50 one by one. As shown in FIG. 9, the cuvette 2 is configured by a brim portion 2a having a diameter D1 (about 10 mm) and a body portion 2b having a diameter D2 (about 8 mm) smaller than the diameter D1. The cuvette 2 has a length of about 30 mm. The brim portion 2a is arranged at one end in the longitudinal direction of the body portion 2b.

Figure 4:
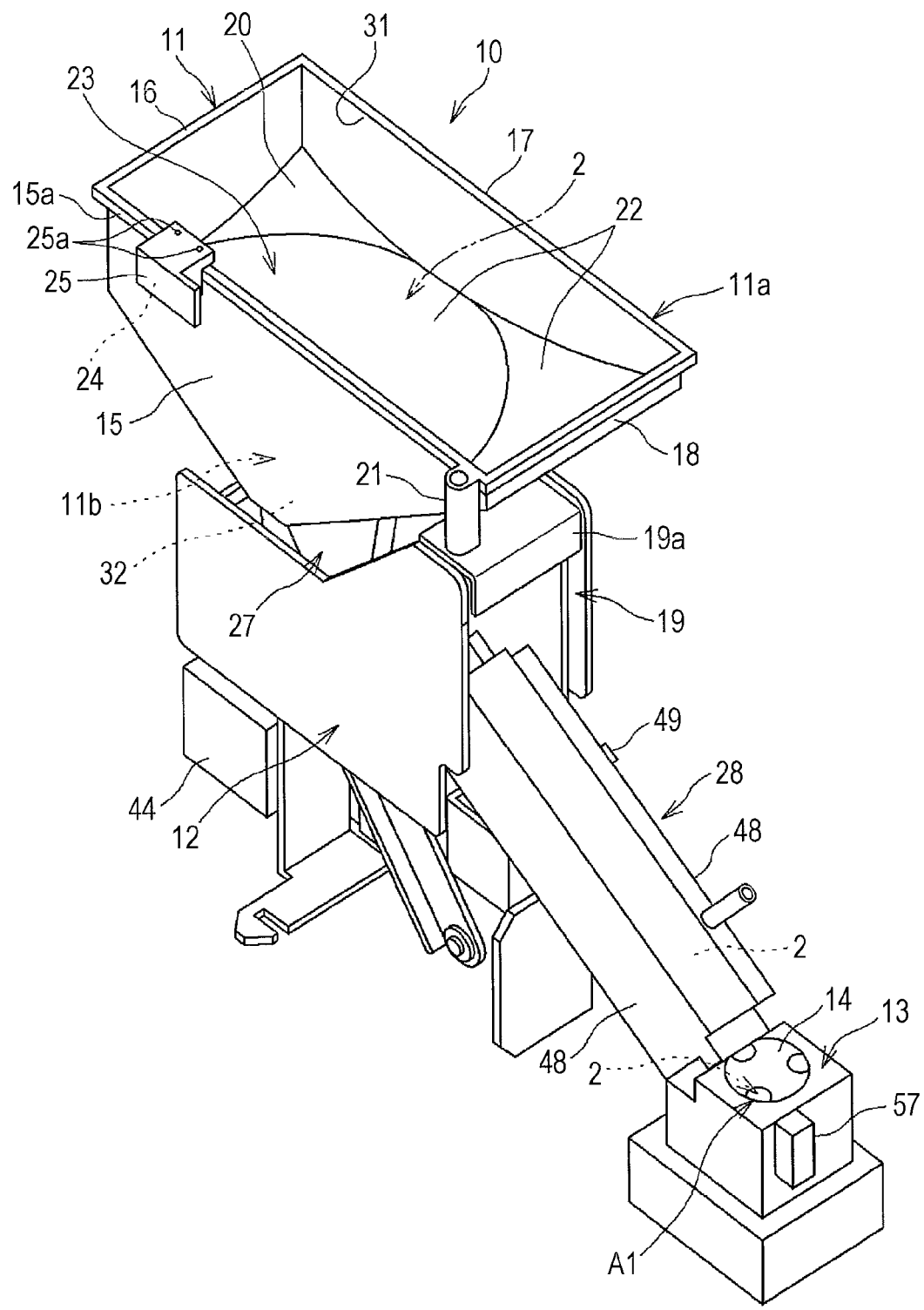
FIG. 4 is a perspective view of a supply mechanism section arranged in the analyzer.

As shown in FIG. 4, the supply mechanism section 10 includes the storage section 11 for storing a plurality of cuvettes 2 input from the input port 5a. In addition to the storage section 11, the supply mechanism section 10 includes a take-out section (take-out mechanism) 12 for taking out the cuvette 2 in the storage section 11 from the storage section 11. Furthermore, the supply mechanism section 10 includes an arrangement unit for arranging the cuvette 2 taken out by the take-out section 12 at a predetermined position A1. The arrangement unit of the present embodiment includes a rotation transfer unit 13 having a rotating body 14 that rotates while holding the cuvette 2. The cuvette 2 positioned at the predetermined position A1 is gripped by the grip portion 55 of the catcher device unit 54 (see FIG. 3) and transported to the detection unit 51.

[Regarding Storage Section 11]

The storage section 11 deposits and stores the input cuvette 2 from the bottom of the storage section 11. The storage section 11 of the present embodiment includes a container made of resin, and is able to store about 300 cuvettes 2, for example.

Figure 5:
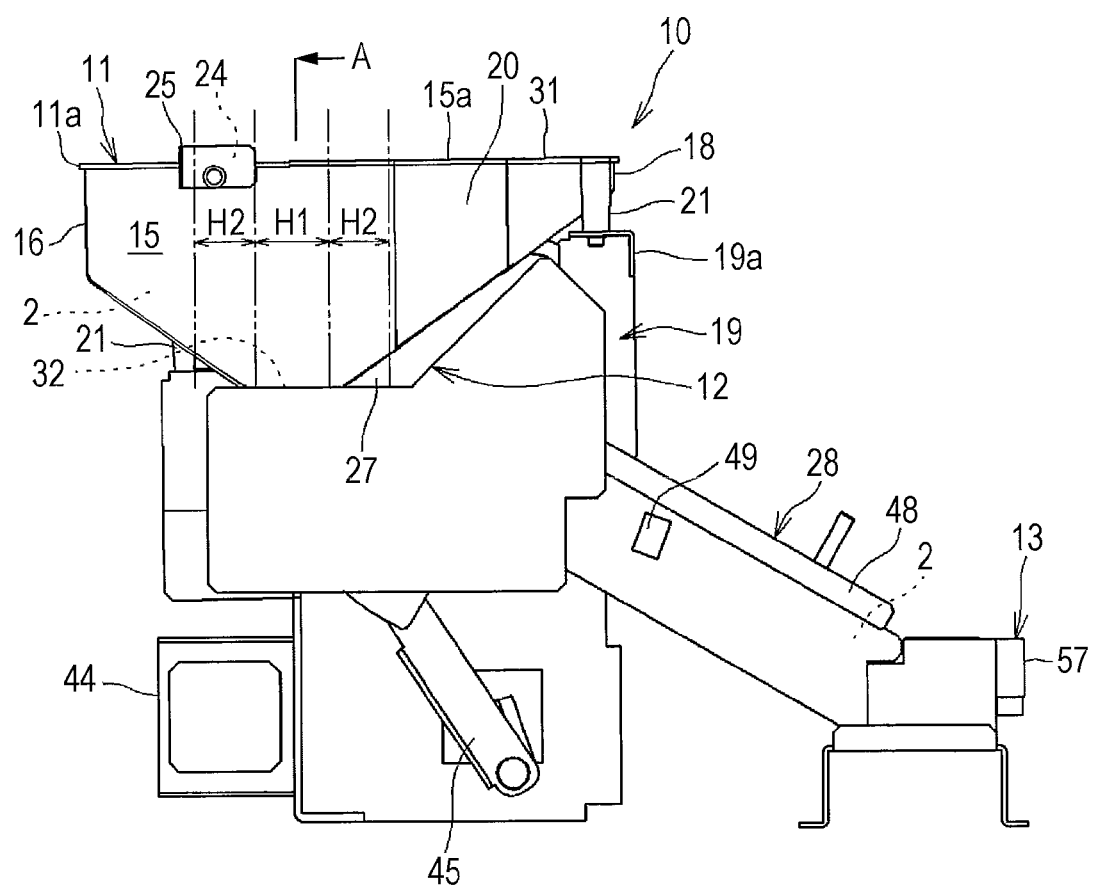
FIG. 5 is a front view of the supply mechanism section.
Figure 6:
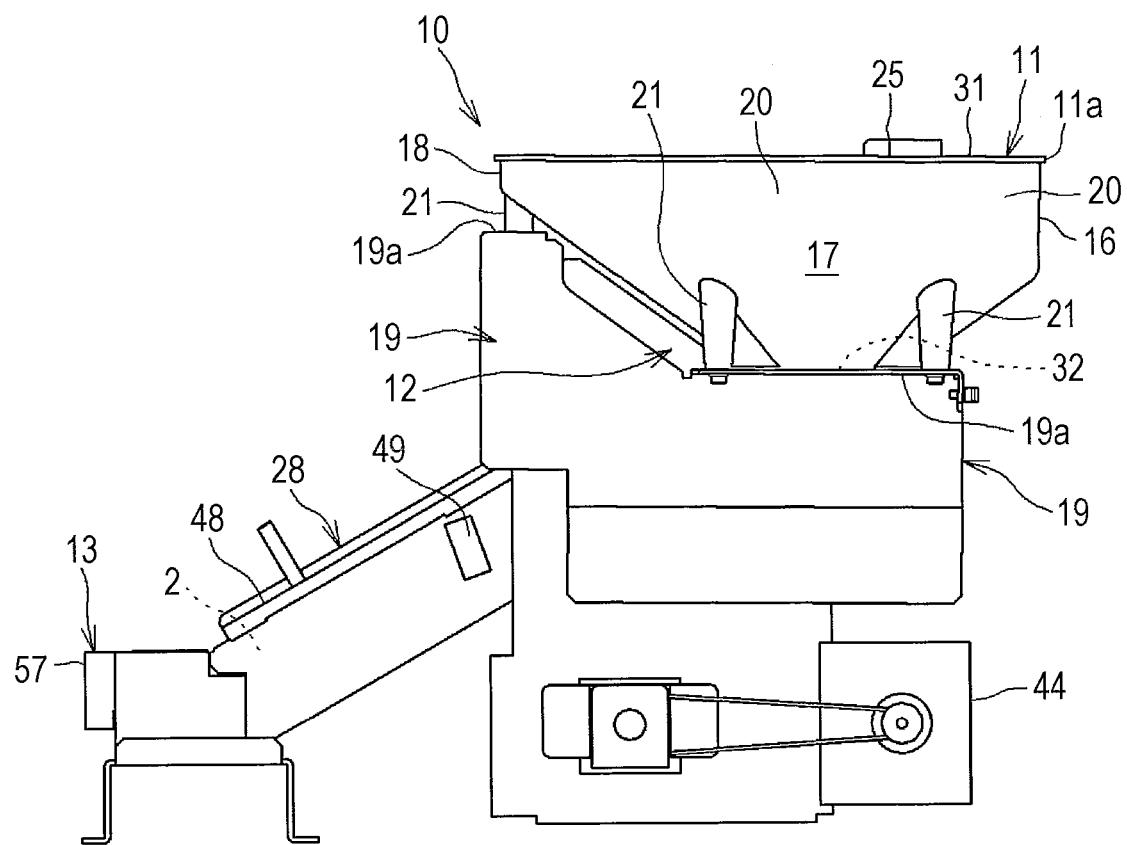
FIG. 6 is a rear view of the supply mechanism section.

The supply mechanism section 10 includes a main body unit 19 for attaching a motor 44 that is to be a drive source of the take-out section 12. The main body unit 19 includes a metal frame 19a having high rigidity. The frame 19a supports the storage section 11 from below. As shown in FIGS. 4, 5, and 6, the storage section 11 includes a container unit 20 for containing and storing the cuvettes 2 on the inner side, and a plurality of (three in the present embodiment) leg units 21 integrally arranged on the outer side of the container unit 20. The storage section 11 is fixed to the main body unit 19 by screw-fitting the leg unit 21 to the frame 19a.

The storage section 11 is formed with a first opening 31 opened toward the upper side. The storage section 11 has a rectangular shape in plan view (see FIG. 7), and includes side walls 15, 16, 17, and 18 that inhibit the stored cuvette 2 from dropping out to the side.

A second opening 32 is also formed on the bottom side of the storage section 11. The second opening 32 has a smaller opening area than the first opening 31. The first opening 31 is an opening through which the cuvette 2 input from the input port 5a passes toward the storage section 11, and the second opening 32 is an opening through which the cuvette 2 retained in the storage section 11 is taken out by the take-out section 12 little by little (one in the present embodiment). To this end, the take-out section 12 is arranged at a position facing the second opening 32.

Thus, the first opening 31 through which the cuvette 2 is input is arranged on an upper part 11a side of the storage section 11, and the second opening 32 through which the cuvette 2 is taken out from the storage section 11 by the take-out section 12 is formed on the bottom side of the storage section 11.

The first opening 31 is set so that the opening area becomes large to an extent that a great number of cuvettes 2 can be simultaneously passed, and the second opening 32 is set so that the opening area becomes smaller than the first opening 31. In particular, the second opening 32 is set so that the opening area becomes small to an extent that one cuvette 2 can be taken out by the take-out section 12. Thus, a great number of cuvettes 2 can be collectively input from the first opening 31 into the storage section 11, and the cuvette 2 can be taken out little by little (one in the present embodiment) from the second opening 32.

The storage section 11 interiorly includes an inclined surface 22 between the upper part 11a where the first opening 31 is formed, and the bottom 11b where the second opening 32 is formed.

Figure 8:
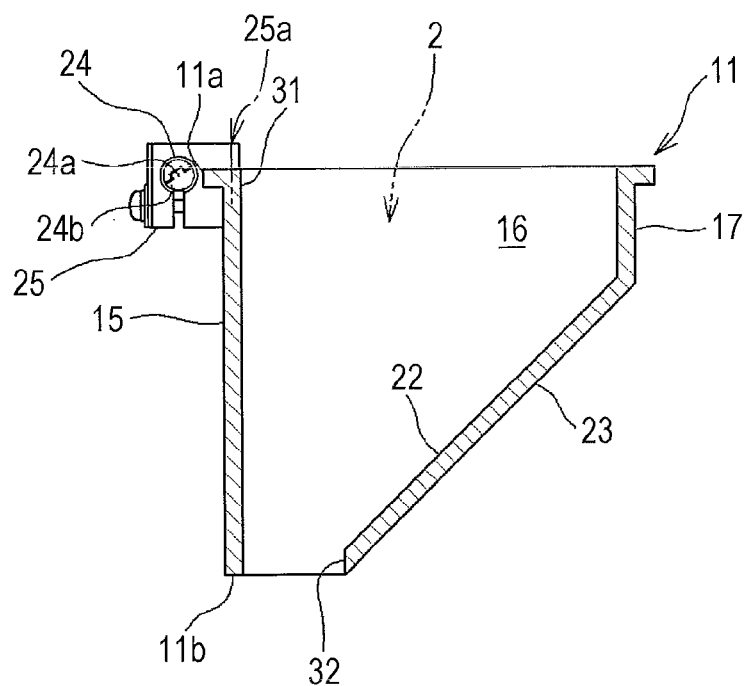
FIG. 8 is a cross-sectional view (cross-sectional view taken along arrow A of FIG. 5) of a storage section.

As shown in FIG. 8, the second opening 32 is formed at the bottom 11b positioned the lowermost in the storage section 11. As shown in FIG. 8 and FIG. 4, the storage section 11 includes an inclined wall 23 having the inclined surface 22 between the bottom 11b and the second to fourth side walls 16 to 18. The first side wall 15 is a wall (planar shaped wall along the vertical place) standing in the vertical direction from the bottom 11b where the second opening 32 is formed, without interposing the inclined surface from the bottom 11b where the second opening 32 is formed. The second opening 32 is arranged to be adjacent to the lower end of the first side wall 15. The first side wall 15 is a perpendicular side wall arranged between the first opening 31 and the second opening 32.

Accordingly, the space where the storage section 11 accommodates the cuvette 2 becomes the region surrounded by the first side wall 15, the inclined wall 23, and the second to fourth side walls 16 to 18. The accommodation space of the storage section 11 has a shape tapered toward the bottom 11b. Thus, since the inclined wall 23 having the inclined surface 22 is arranged, the storage section 11 can easily gather the great number of cuvettes 2 input from the first opening 31 toward the second opening 32 side arranged at the bottom 11b. The gathered cuvettes 2 can be arranged along the first side wall 15, and the cuvette 2 is taken out little by little by the take-out section 12 from the second opening 32 arranged in the vicinity of the side wall 15. The configuration of the take-out section 12 will be described later.

[Regarding Vibration Unit 24]

As shown in FIG. 4, the supply mechanism section 10 includes a vibration unit 24 for vibrating the storage section 11. The vibration unit 24 stimulates the movement of the cuvette 2 accommodated in the storage section 11 by vibrating the storage section 11. The operation of the vibration unit 24 is controlled by the control unit 7. The vibration unit 24 includes a vibration motor, and is attached to the side wall of the storage section 11 by an attachment member 25.

Figure 7:
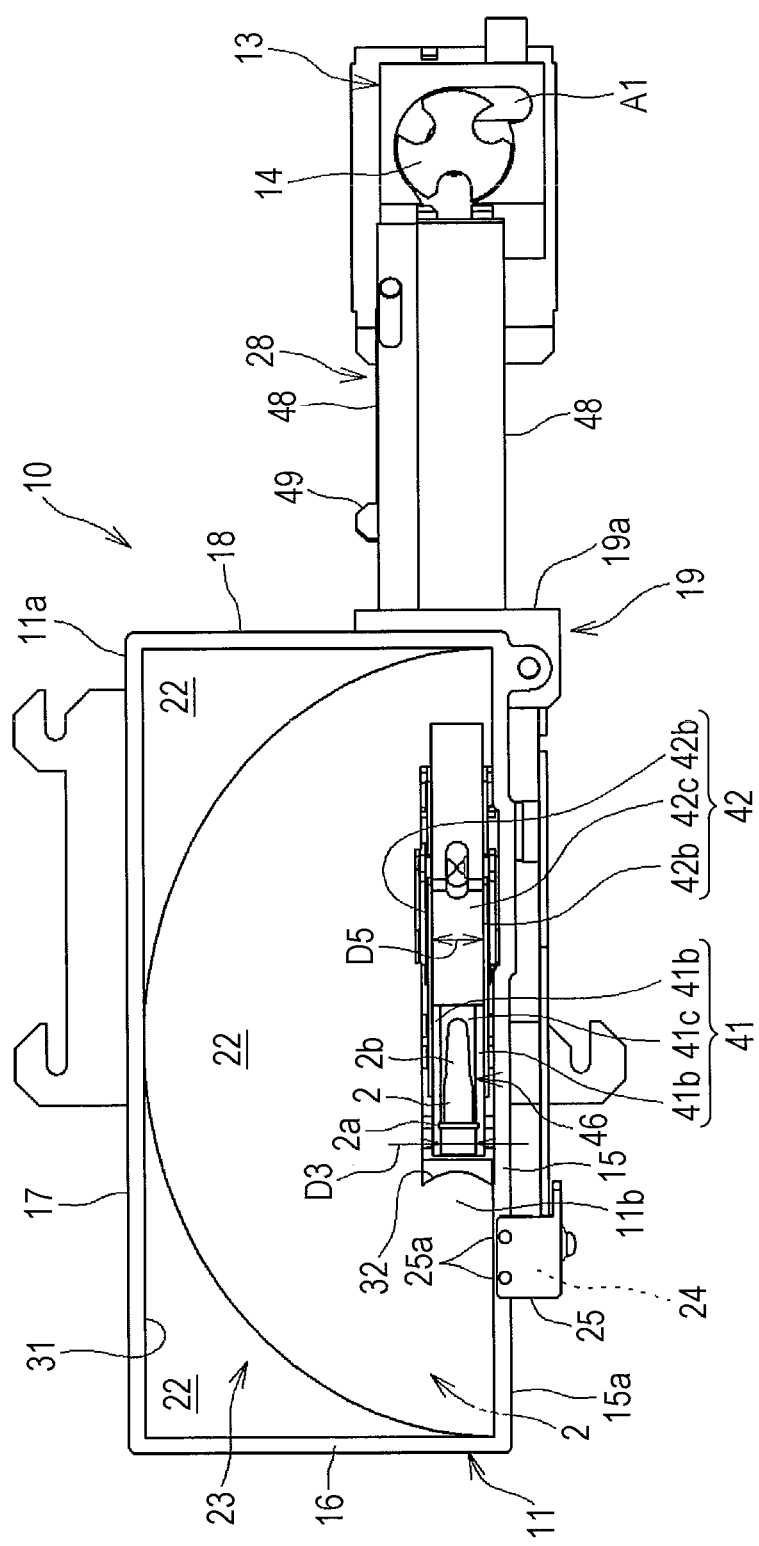
FIG. 7 is a plan view of the supply mechanism section.

As shown in FIG. 7, the second opening 32 is arranged at a deviated position near the first side wall 15 side and not at the middle of the bottom of the storage section 11 in plan view. In the present embodiment, the vibration unit 24 is attached to the first side wall 15 closest to the second opening 32 and adjacent to the second opening 32 of the side walls 15 to 18, and vibrates the side wall 15 with the largest amplitude.

That is, the second opening 32 is arranged at a position adjacent to the first side wall 15, the position being a part of the side wall of the storage section 11. The vibration unit 24 is attached to the first side wall 15 adjacent to the second opening 32. Thus, even if the cuvettes are tangled and are difficult to move at the periphery of the second opening 32, the tangled state can be resolved by greatly vibrating the first side wall 15 adjacent to the second opening 32. The vibration unit 24 is preferably attached in a range (range of H1 shown in FIG. 5) adjacent to a virtual space on a vertically upper side of the second opening 32 or a range (range of H2 shown in FIG. 5) from the relevant range (H1) to a position shifted in a horizontal direction by a longitudinal dimension of one cuvette 2 of the first side wall 15 where the second opening 32 is adjacently arranged. In this case as well, the vibration unit 24 is attached to an outer surface side of the first side wall 15.

Furthermore, the storage section 11 is supported and fixed to the frame 19a of the main body unit 19 from the bottom, whereas the vibration unit 24 is attached to the upper part 11a where the first opening 31 is formed in the storage section 11. Thus, since the storage section 11 is supported by the main body unit 19 from the bottom and the vibration unit 24 applies vibration to the upper part 11a of the storage section 11, the storage section 11 can be efficiently vibrated.

The rigidity of the storage section 11 is relatively low at the opening. In particular, the first opening 31 side having a large opening area has a lower rigidity than the second opening 32 side. The storage section 11 can be efficiently vibrated by attaching the vibration unit 24 to the upper part 11a where the first opening 31 is formed.

The storage section 11 has a rectangular shape in plan view (see FIG. 7), and the vibration unit 24 is attached to the first side wall 15, which is the side wall on the long side. In particular, the first side wall 15 has a planar plate shape, and has the largest area among the side walls. All of the side walls 15 to 18 are formed to have the same thickness. The side walls 16, 17, and 18, to which the vibration unit 24 is not attached, have a relatively high rigidity since the inclined wall 23 functions as a reinforcement rib, whereas the first side wall 15 has a low rigidity compared to the side walls 16, 17, and 18. The vibration of great amplitude, which is an effective vibration, can be applied by attaching the vibration unit 24 to the first side wall 15. The vibration unit 24 is attached at a position closer to the middle in the horizontal direction, that is, closer to the middle of the long side in the first side wall 15.

The vibration unit 24 is attached to the side wall 15 so that the maximum amplitude is generated mainly in the plate thickness direction of the side wall 15. The vibration unit 24 includes a vibration motor. The vibration motor is a motor having a cylindrical outer appearance, and is an eccentric motor, in which a spindle 24c is attached to an output shaft 24a so as to be eccentric with respect to a center line of the output shaft 24a. The vibration motor is fixed to the side wall 15 such that the axial direction (direction orthogonal to the plane of drawing in the case of FIG. 8) of the output shaft 24a of the motor becomes orthogonal to the plate thickness direction of the side wall 15.

The vibration unit 24 is attached to the outer surface side of the side wall 15, and does not form a protrusion on the inner surface side of the storage section 11. The attachment member 25 is fixed to a flange portion 15a, arranged at the upper surface of the side wall 15, by a locking screw 25a (see FIG. 4, FIG. 7, FIG. 8) from above. Thus, the locking screw 25a does not project out toward the inner surface side of the storage section 11. Thus, the inner surface of the storage section 11 does not form protrusions, and the like, which cause retention of the cuvettes 2, and the inner surface of each wall is configured to be as smooth as possible.

[Regarding Take-Out Section 12]

In FIG. 4, the take-out section 12 includes a supporting member and an operation unit 27 for taking out the cuvette 2 one by one from the second opening 32 of the storage section 11, and an alignment unit 28 for aligning the cuvettes 2 taken out by the supporting member and the operation unit 27. The supporting member will be described later. The supply mechanism section 10 includes the rotation transfer unit 13 as an arrangement unit for arranging the cuvette 2 taken out by the take-out section 12 at the predetermined position A1. The rotation transfer unit 13 accommodates the cuvettes 2 aligned by the alignment unit 28 one by one, and transfers the same to the predetermined position A1.

Figure 10:
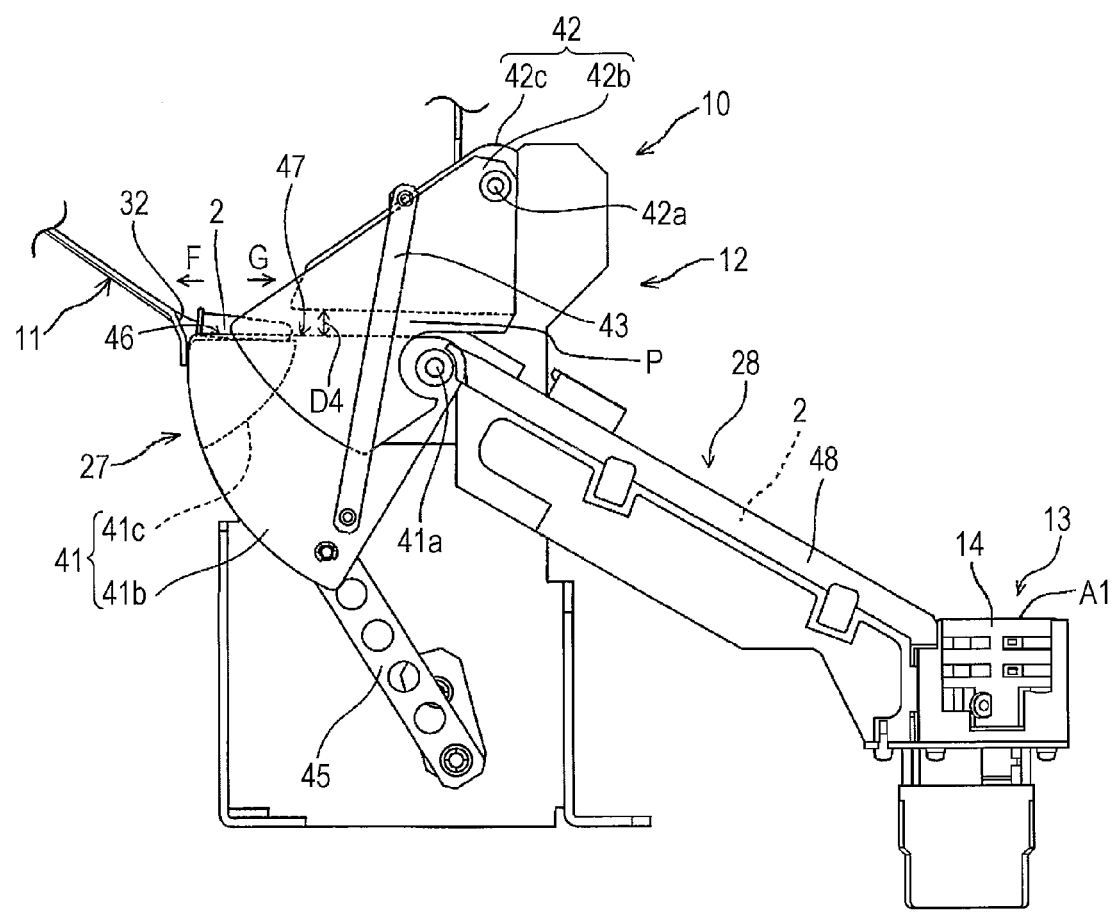
FIG. 10 is a side view describing a take-out section.
Figure 11:
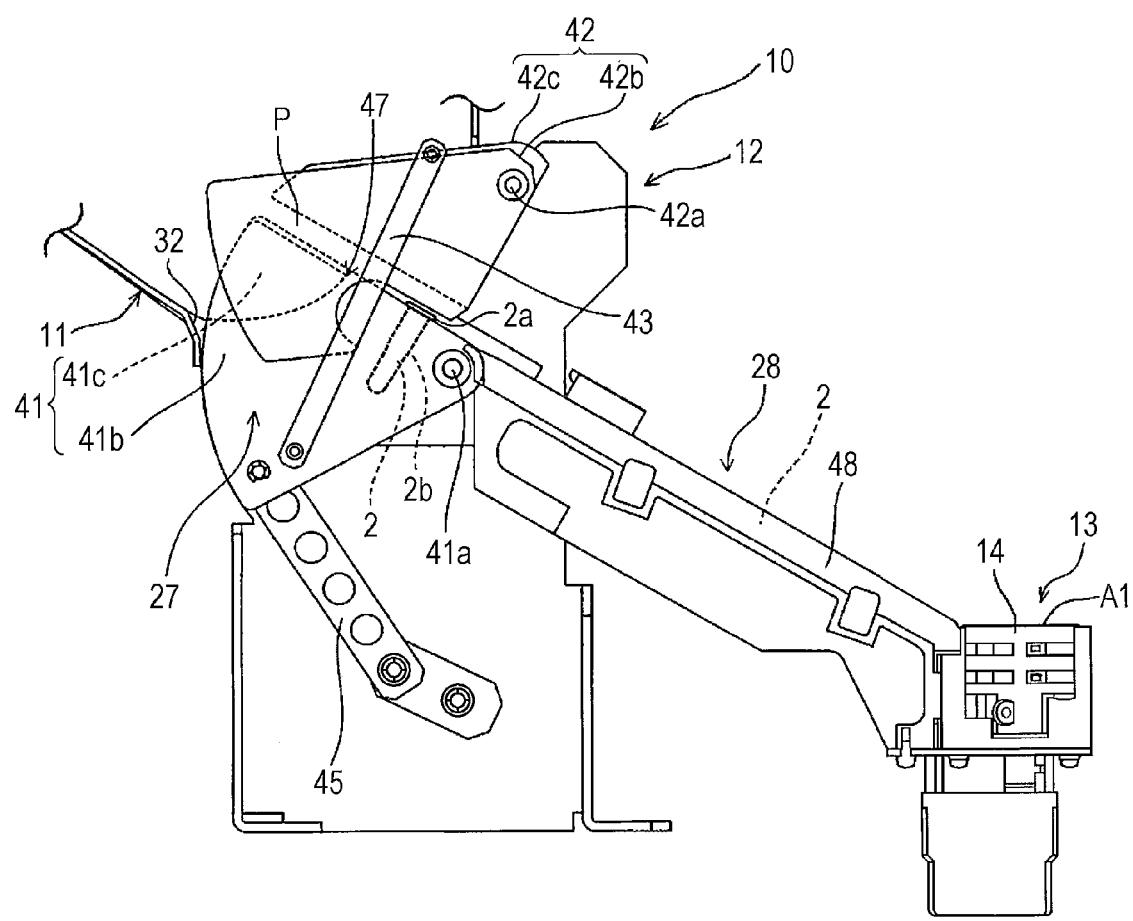
FIG. 11 is a side view describing the take-out section.

FIG. 11 shows the middle of the operation of the supporting member and the operation unit 27. As shown in FIG. 10 and FIG. 11, the take-out section 12 includes, for the supporting member, a swing rail 41 that can be swung with a pivot shaft 41a as a center. The take-out section 12 includes, for an auxiliary member of the supporting member, a swing guide 42 that can be swung with a different pivot shaft 42a as a center. The take-out section 12 includes, as the operation unit 27, a link 43 that couples and cooperatively operates the swing rail 41 and the swing guide 42, The motor 44 (see FIG. 4), and an arm (e.g., crank arm) 45 that transmits the drive force of the motor 44 to the swing rail 41. The arm 45 is rotated by the rotating motor 44, whereby the swing rail 41 and the swing guide 42 are reciprocately swung. The swing rail 41 is arranged at the bottom 11b of the storage section 11, that is, at the forming position of the second opening 32, and is exposed from the opening 32. One cuvette 2 positioned the lowermost in the storage section 11 can be mounted on the swing rail 41 (state of FIG. 10). The position of the cuvette 2 is referred to as a sending position 46.

The swing rail 41 includes a pair of fan-shaped plates 41b, and a spacer 41c fixed while being sandwiched between the fan-shaped plates 41b. As shown in FIG. 7, a distance of the pair of fan-shaped plates 41b (thickness of the spacer 41c) D3 is smaller than the diameter D1 of the brim portion 2a of the cuvette 2 (see FIG. 9) and larger than the diameter D2 of the body portion 2b.

The swing guide 42 includes a pair of guide plates 42b arranged to make contact with the outer sides of the pair of fan-shaped plates 41b of the swing rail 41, and a spacer 42c fixed while being sandwiched by the guide plates 42b. A passage P, through which the cuvette 2 can pass, is formed between the swing rail 41 and the swing guide 42.

As shown in FIG. 10, a distance D4 between the spacer 41c of the swing rail 41 and the spacer 42c of the swing guide 42 is larger than the diameter D1 of the brim portion 2a of the cuvette 2 (see FIG. 9) but is formed to a size that does not allow two cuvettes 2 to pass. Furthermore, as shown in FIG. 7, a distance D5 of the pair of guide plates 42b is larger than the diameter D1 of the brim portion 2a of the cuvette 2 but is formed to a size that does not allow two cuvettes 2 to pass. Thus, only one cuvette 2 will be arranged at the sending position 46 (see FIG. 10 and FIG. 7).

As shown in FIG. 10, the direction of the cuvette 2 becomes parallel to the swing rail 41 at the sending position 46. The open end of the cuvette 2 may be directed in any direction, the direction of the arrow F or the direction of the arrow G. As shown in FIG. 11, the spacer 41c of the swing rail 41 is cut at a position 47 in the middle of the fan-shaped plate 41b, and has a terminating surface. Thus, the close end of the cuvette 2 lowers to the lower side by its own weight at the position 47 when the cuvette 2 moves on the swing rail 41. The distance D3 (see FIG. 7) is smaller than the diameter D1 of the brim portion 2a of the cuvette 2 (see FIG. 9) and larger than the diameter D2 of the body portion 2b, and thus the brim portion 2a is supported by the pair of fan-shaped plates 41b, as shown in FIG. 11. Thus, in the operation unit 27, the open end of the cuvette 2 is made upward in the course of passing the cuvette 2 through the passage P.

Therefore, the swing rail 41, which is the supporting member, has a gap of a predetermined width (D3) for supporting the brim portion 2a of the cuvette 2, and the operation unit 27 can swing and diagonally displace the swing rail 41 and the swing guide 42 that support the brim portion 2a of the cuvette 2. Therefore, when the swing rail 41 and the swing guide 42 are swung with the cuvette 2 at the sending position 46, the cuvette 2 passes through the passage P as shown in FIG. 10 and FIG. 11. The cuvette 2 is received by the alignment unit 28, and the cuvette 2 is supplied to a transportation rail 48 of the alignment unit 28.

The transportation rail 48 configures the passage for guiding and aligning the cuvettes 2 to the rotation transfer unit 13. The transportation rails 48 are rail members arranged parallel to each other with a distance smaller than the diameter D1 of the brim portion 2a of the cuvette 2 (see FIG. 9) and larger than the diameter D2 of the body portion 2b of the cuvette 2. The cuvette 2 that passed through the passage P is moved while slidably dropping toward the rotation transfer unit 13 with the brim portion 2a placed on the upper surface of the pair of transportation rails 48. A predetermined number of cuvettes 2 is held with being lined in one row on the transportation rail 48.

Therefore, the take-out section 12 includes the operation unit 27 for performing the operation of taking out the cuvette 2 stored in the storage section 11 one by one and the alignment unit 28 for aligning the cuvettes 2 taken out by the operation unit 27 at the downstream thereof. According to the take-out section 12, a great number of cuvettes 2 input without thinking to the storage section 11 can be taken out from the storage section 11 and aligned on the downstream side of the storage section 11, and the cuvette 2 can be supplied to the rotation transfer unit 13 one by one. As a result, the task of taking out the cuvette 2 one by one from the rotation transfer unit 13 by the catcher device unit 54 is facilitated.

The supply mechanism section 10 includes a first sensor 49 (see FIG. 4) for detecting the cuvette 2 taken out from the storage section 11 by the take-out section 12. The sensor 49 of the present embodiment detects the cuvettes 2 lined on the transportation rail 48. The sensor 49 is a contactless sensor, and is able to detect the cuvette 2 positioned at the top, which is one of the predetermined number of cuvettes 2 held in a line on the transportation rail 48.

That is, the transportation rail 48 is able to hold the cuvette 2 by a predetermined number in a line, where, when the number of cuvettes 2 held on the transportation rail 48 reaches a predetermined number (e.g., 10), the sensor 49 detects such state.

A signal output from the sensor 49 becomes a trigger to start the operation and a trigger to stop the operation of the vibration unit 24. In a case where the cuvette 2 is not detected by the sensor 49 even if the take-out operation of the cuvette 2 by the take-out section 12 is carried out, the control unit 7 vibrates the storage section 11 with the vibration unit 24. A specific example of such control will be described later.

The rotation transfer unit 13 includes the rotating body 14 formed with a pocket for receiving the cuvette 2 slidably dropped from the transportation rail 48 and positioned at the lowermost position. The rotation transfer unit 13 rotates the rotating body 14 to rotatably transfer the cuvette 2 in the pocket to a position (predetermined position A1) where the cuvette 2 can be held by the grip portion 55 of the catcher device unit 54. The cuvette 2 transferred to the predetermined position A1 is gripped by the grip portion 55, and transported to the detection unit 51. The sample is supplied to the cuvette 2, and furthermore, the reagent is supplied to the cuvette 2 so that the sample and the reagent are mixed in the cuvette 2, and thereafter, the optical analysis of the sample is carried out.

[Regarding Description of Operation of Supply Mechanism Section 10]

Figure 12:
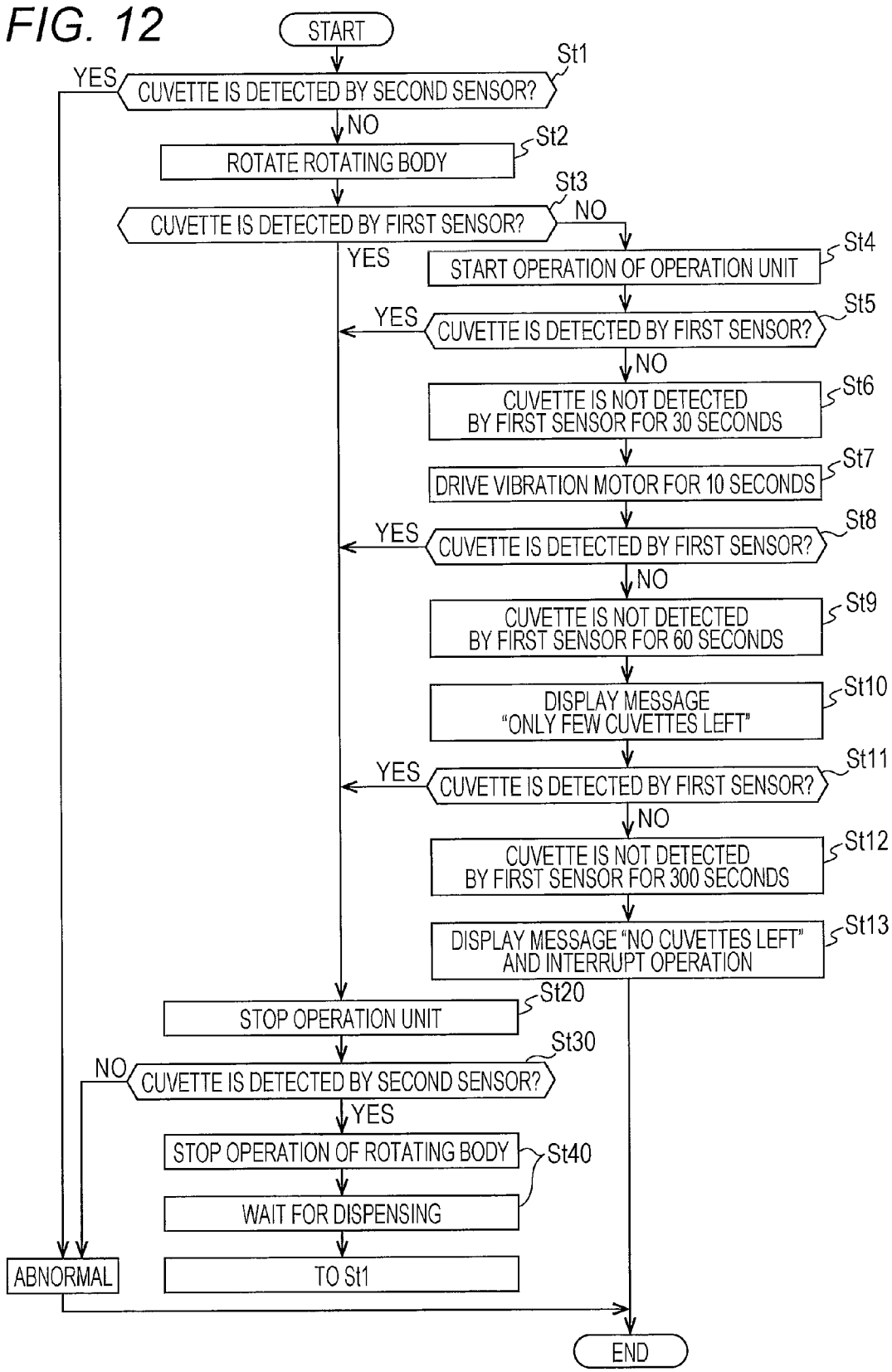
FIG. 12 is a flowchart describing the operation of the supply mechanism section.

The operation of the supply mechanism section 10 having the above configuration will be described according to the flowchart shown in FIG. 12. The operation of the supply mechanism section 10 starts when the cuvette 2 at the predetermined position A1 of the rotation transfer unit 13 (see FIG. 4) is taken out by the grip portion 55 (see FIG. 3) of the catcher device unit 54. The control of the operation of each mechanism section is carried out by the control unit 7.

The rotation transfer unit 13 includes the second sensor 57 (see FIG. 4) to detect the cuvette 2 at the predetermined position A1. When the cuvette 2 is taken out by the grip portion 55 and the cuvette 2 is not detected by the second sensor 57 (case of "NO" in step St1 of FIG. 12), the rotation transfer unit 13 rotates the rotating body 14 (step St2). The cuvette 2 at the lowermost position of the transportation rail 48 thereby automatically enters to the empty pocket of the rotating body 14 by its own weight. As a result, the cuvettes 2 lined on the transportation rail 48 decreases by one.

The first sensor 49 is then in a state of not detecting the cuvette 2 (case of "NO" in step St3), the operation of the operation unit 27 is started (step St4), and the operation of taking out the cuvette 2 from the storage section 11 is carried out. The take-out operation is repeatedly carried out until the first sensor 49 detects the cuvette 2, and the operation unit 27 is stopped (step St20) when the first sensor 49 detects the cuvette 2 (case of "YES" of step St5).

If a state in which the detection of the cuvette 2 by the first sensor 49 is not carried out is continued for a first predetermined time (30 seconds in the present embodiment) (step St6) after the start of operation of the operation unit 27, the vibration unit 24 is operated for a constant time (10 seconds in the present embodiment) after elapse of a predetermined time (step St7). The control unit 7 has a timer function for measuring time.

In other words, if the sensor 49 does not detect the cuvette although the operation unit 27 is operating, the cuvettes have a possibility of being tangled and not being able to be taken out in the storage section 11. If a state in which the first sensor 49 does not detect the cuvette for a first predetermined time (30 seconds) is continued, the control unit 7 vibrates the storage section 11 with the vibration unit 24 (step St7). The tangling of the cuvettes possibly occurring in the storage section 11 thus can be resolved. When the first sensor 49 detects the cuvette 2 (case of "YES" of step St8), the operation unit 27 is stopped (step St20).

On the contrary, if the state in which the detection of the cuvette 2 by the first sensor 49 is not carried is continued for a second predetermined time (60 seconds in the present embodiment) (step St9) after the start of the operation of the operation unit 27, information indicating that the cuvette 2 is decreasing is reported to the user by being displayed as characters on the output section 6 (step St10).

In other words, the reason why the sensor 49 cannot detect the cuvette 2 includes a case in which the storage section 11 is empty in addition to a case in which the cuvettes 2 are tangled in the storage section 11 and thus cannot be taken out. Thus, if the sensor 49 cannot detect the cuvette even after the storage section 11 is vibrated by the vibration unit 24, the storage section 11 has a high possibility of being empty, and hence the output section 6 outputs information urging replenishment of the cuvette in the storage section 11 to call attention to the user. For example, a message "only few cuvettes left" is displayed on the output section 6 as the information urging replenishment (step St10).

The detection of the cuvette by the sensor 49 is repeatedly executed (step St11), and although the cuvettes are tangled in the storage section 11 and cannot be taken out; however, this problem is resolved with a delay, so that when the cuvette is taken out from the storage section 11 by the operation of the operation unit 27, the sensor 49 detects the cuvette (case of "YES" in step St11) and the operation unit 27 is stopped (step St20).

However, if the state in which the detection of the cuvette 2 by the first sensor 49 is continued for a third predetermined time (300 seconds in the present embodiment) (step St12) after the start of the operation of the operation unit 27, information indicating that no cuvette 2 is left is reported to the user by being displayed as characters on the output section 6 (step St13). For example, a message "no cuvettes is left" is displayed on the output section 6.

The third predetermined time is a value obtained by multiplying the number of cuvettes (10 in the present embodiment) scheduled to be normally aligned on the transportation rail 48 to a cycle time (30 seconds in the present embodiment) of the operation in which the grip portion 55 of the catcher device unit 54 takes out the cuvette 2, and with such setting, the information indicating that no cuvettes 2 is left can be output to the output section 6 at the timing when all the cuvettes of the supply mechanism section 10 are transported out from the transportation rail 48.

When the second sensor 57 detects the presence of the cuvette at the predetermined position A1 of the rotation transfer unit 13 (case of "YES" in step St30) after the operation unit 27 is stopped in step St20 in each operation already described, the rotating body 14 is in a stopped state and the taking out of the cuvette 2 by the grip portion 55 of the catcher device unit 54 is put to standby (step St40).

Therefore, according to the analyzer 1 of the present embodiment, even if a great number of cuvettes 2 are input without thinking to the storage section 11 and the cuvettes are squeezed together so that the plurality of cuvettes 2 are tangled and are difficult to be moved due to the friction between each other in the storage section 11, the movement of the cuvette 2 in the storage section 11 can be stimulated by vibrating the storage section 11 with the vibration unit 24 (step St7). Thus, the take-out section 12 is able to take out the cuvette 2 from the storage section 11, and the cuvette 2 can be stably supplied to the downstream side (rotation transfer unit 13, and furthermore, the analyzing section 50).

The analyzer 1 of the present embodiment includes the analyzing section 50 for analyzing the sample, which is an analyzing specimen, using the cuvette, which is a disposable part, supplied by the supply mechanism section 10. Therefore, the sample can be analyzed by the analyzing section 50 using the cuvette 2 stably supplied by the supply mechanism section 10, whereby the analyzing operation can be efficiently performed.

If the sensor 49 does not detect the cuvette even after the storage section 11 is vibrated by the vibration unit 24 (step St9), the storage section 11 has a high possibility of being empty, and hence the output section 6 outputs the information urging the replenishment of the cuvette in the storage section 11 (step St10). Therefore, attention can be called to the user.

In the present embodiment, the vibration unit 24 includes a vibration motor. Therefore, the storage section 11 can be vibrated with a simple configuration. In the present embodiment, the vibration motor is a motor having a cylindrical outer appearance, but is not limited thereto. The vibration unit 24 may be other than the vibration motor. Furthermore, a configuration including a motor, and a member that is attached to the output shaft of the motor and that intermittently makes contact with the wall of the storage section when the output shaft is rotated, so as to hit the wall of the storage section may be adopted instead of the vibration unit 24.

There can considered the supply mechanism section including a first storage section having a large capacity and a second storage section having a small capacity, where the cuvettes stored in great amount in the first storage section are transported to the second storage section little by little and the cuvettes are taken out from the second storage section one by one; however, in this case, two storage sections are necessary. Thus, this is difficult to apply on a small analyzer, but the present embodiment is suited for the small analyzer since only a single storage section 11 is arranged.

In the present embodiment, the storage section 11 is fixed to the main body unit 19 (see FIG. 4), but a drive mechanism having a swing supporting point (not shown) provided between a part of the storage section 11 and the main body unit 19 to swing the storage section 11 may be adopted. In this case, if the detection of the cuvette by the sensor 49 is not carried out, the vibration unit 24 is operated and the storage section 11 is swung. Thus, the tangling of the cuvettes can be more effectively resolved.

The analyzer 1 of the present embodiment is not limited to the illustrated modes, and other modes may be adopted within the scope of the invention. In the present embodiment, the disposable part stored in the storage section 11 and used for analysis is the cuvette 2 (see FIG. 9) for mixing the reagent and the sample. However, the disposable part may be other objects, for example, a disposable tip attached to the distal end of the pipette for aspirating or discharging the sample and the reagent, and the like. Furthermore, in the present embodiment, one control unit 7 performs the analyzing process of the sample and also performs the operation control of each unit such as the vibration unit 24, and the like, but the analyzing process of the sample and the operation control of the vibration unit 24, and the like may be carried out by another control unit.

In the present embodiment, the analyzer 1 is a blood clotting analyzer, but is not limited thereto, and the analyzer 1 may be an apparatus for analyzing any biological specimen for the sample. For example, the analyzer 1 may be an immune analyzer or a biochemical analyzer for measuring blood serum, a blood cell counting apparatus for counting blood cells in the blood, a urine analyzer for analyzing urine, or an analyzer for analyzing the bone marrow fluid.

What is claimed is:

1. An analyzer comprising:
    a storage section configured to store a plurality of randomly arranged parts to be used in analyzing samples, the storage section defines a first opening at a top most region of the analyzer configured to receive one or more of the plurality of randomly arranged parts;
    a take-out section configured to remove one or more of the randomly arranged parts from the storage section;
    a transportation rail configured to guide the one or more randomly arranged parts removed by the take-out Section to an analyzing section;
    a sensor positioned on the transportation rail configured to detect the randomly arranged parts taken out from the storage section;
    a vibration unit attached to a region of the storage section nearest the first opening, the vibration unit is configured to vibrate the storage section to transmit vibration to the randomly arranged parts in the storage section for a predetermined amount of time based on a detection result by the sensor, wherein vibration of the randomly arranged parts prevents the randomly arranged parts from becoming jammed within the storage section and, thereby, facilitates removal, by the take-out section, of all the randomly arranged parts from the storage section; and
    wherein the analyzing section is configured to analyze a sample using at least one of the plurality of parts taken out by the take-out section.

2. The analyzer according to claim 1, wherein
    the storage section includes a side wall; and
    the vibration unit is attached to the side wall of the storage section.

3. The analyzer according to claim 1, further comprising:
    a main body unit configured to support the storage section from below.

4. The analyzer according to claim 1, wherein
    the storage section defines a second opening arranged at a bottom of the storage section and configured to have an opening area smaller than the first opening.

5. The analyzer according to claim 4, wherein the take-out section is arranged at a position facing the second opening.

6. The analyzer according to claim 4, wherein the vibration unit is attached to a portion formed with the first opening in the upper part of the storage section.

7. The analyzer according to claim 4, wherein
    the storage section includes at least one perpendicular side wall between the first opening and the second opening; and
    the vibration unit is attached to the perpendicular side wall adjacent to the second opening.

8. The analyzer according to claim 7, wherein the storage section includes an inclined surface at an inner surface between the first opening and the second opening.

9. An analyzer comprising:
    a storage section configured to store a plurality of randomly arranged parts to be used in analyzing samples;
    a take-out section configured to remove one or more of the randomly arranged parts from the storage section;
    a vibration unit configured to vibrate the storage section to transmit vibration to the randomly arranged parts in the storage section, wherein vibration of the randomly arranged parts prevents the randomly arranged parts from becoming jammed within the storage section and, thereby, facilitates removal, by the take-out section, of all the randomly arranged parts from the storage section;

an analyzing section configured to analyze a sample using at least one of the plurality of parts taken out by the take-out section;

a transportation rail configured to guide the one or more randomly arranged parts removed by the take-out section to the analyzing section;

a sensor positioned on the transportation rail configured to detect one or more of the plurality of randomly arranged parts taken out from the storage section by the take-out section; and a control unit programmed to control the operation of the vibration unit; wherein when the sensor does not detect one or more of the plurality of randomly arranged parts after the take-out section attempts to perform an operation for removing one or more of the randomly arranged parts from the storage section, the control unit is further configured to cause the vibration unit to vibrate the storage section for a predetermined amount of time.

10. The analyzer according to claim 9, wherein the control unit is further programmed to cause the vibration unit to vibrate the storage section when a state in which the sensor does not detect one or more of the plurality of randomly arranged parts is continued for a predetermined time.

11. The analyzer according to claim 9, further comprising:
an output section configured to output information; wherein
the output section outputs information urging replenishment of one or more of the randomly arranged parts when the storage section is vibrated by the vibration unit but one or more of the plurality of randomly arranged parts is not detected by the sensor.

12. The analyzer according to claim 1, further comprising
a grip portion configured to grip one or more of the plurality of randomly arranged parts taken out from the storage section by the take-out section one by one and transport the one or more of the plurality of randomly arranged parts to the analyzing section; wherein
the analyzing section analyzes the sample using at least one of the plurality of randomly arranged parts transported by the grip portion.

13. The analyzer according to claim 1, wherein
each of the plurality of randomly arranged parts includes a brim portion in the vicinity of one end in a longitudinal direction; and
the take-out section includes,
a supporting member having a gap of a predetermined width to support the brim portion,
an operation unit configured to diagonally displace the supporting member supporting the brim portion, and
an alignment unit configured to receive one or more of the plurality of randomly arranged parts from the supporting member diagonally displaced by the operation unit and align the received one or more of the plurality of randomly arranged parts.

14. The analyzer according to claim 1, wherein the vibration unit includes a vibration motor.

15. The analyzer according to claim 1, wherein the plurality of randomly arranged parts is a plurality of cuvettes, each of which being for mixing a reagent and a sample.

16. The analyzer according to claim 1, wherein the storage section includes a container configured to accommodate the plurality of randomly arranged parts.

17. The analyzer according to claim 1, further comprising:
a main body unit configured to support the storage section; and
a swing supporting point arranged between a part of the storage section and the main body unit, and configured to support the swinging storage section.

18. An analyzing method comprising:
attempting to remove one or more of a plurality of randomly arranged parts from a storage section, the storage section storing a plurality of randomly arranged parts to be used in analyzing samples;
determining, by a sensor, whether one or more of the plurality of randomly arranged parts is successfully removed from the storage section; wherein the sensor is positioned on a transportation rail that is positioned between a take-out section configured to remove one or more of the randomly arranged parts from the storage section and an analyzing section configured to detect the randomly arranged parts taken out from the storage section;
when one or more of the plurality of randomly arranged parts are not successfully removed from the storage section, activating a vibrator for vibrating the storage section for a predetermined amount of time based on a detection result by the sensor to thereby vibrate the plurality of randomly arranged parts in the storage section to thereby prevent the randomly arranged parts from becoming jammed within the storage section; and
analyzing a sample using at least one of the plurality of randomly arranged parts removed from the storage section.

\* \* \* \* \*